| (12) | United States Patent | (10) Patent No.: | US 7,530,951 B2 |
|---|---|---|---|
| | Fehre et al. | (45) Date of Patent: | May 12, 2009 |

(54) METHOD FOR GENERATING A THREE-DIMENSIONAL ULTRASOUND IMAGE

(75) Inventors: Jens Fehre, Hausen (DE); Bernd Granz, Oberasbach (DE)

(73) Assignee: Siemens Aktiengesellschaft, Munich (DE)

( * ) Notice: Subject to any disclaimer, the term of this patent is extended or adjusted under 35 U.S.C. 154(b) by 550 days.

(21) Appl. No.: 10/776,088

(22) Filed: Feb. 11, 2004

(65) Prior Publication Data

US 2004/0220476 A1 Nov. 4, 2004

(30) Foreign Application Priority Data

Feb. 11, 2003 (DE) ............................... 103 05 603

(51) Int. Cl.
*A61B 8/06* (2006.01)
(52) U.S. Cl. .................... 600/459; 600/437; 600/439; 600/443; 600/447; 600/458; 601/2; 601/3
(58) Field of Classification Search ............... 600/431, 600/439, 443, 447, 459, 407, 413, 428, 437, 600/454–456, 458, 462–463; 601/4, 2–3
See application file for complete search history.

(56) References Cited

U.S. PATENT DOCUMENTS

| 4,526,168 | A | * | 7/1985 | Hassler et al. .................. 601/4 |
|---|---|---|---|---|
| 4,962,754 | A | | 10/1990 | Okazaki |
| 5,156,152 | A | * | 10/1992 | Yamazaki et al. ............ 600/454 |
| 5,689,576 | A | * | 11/1997 | Schneider et al. ............ 382/124 |
| 5,876,342 | A | | 3/1999 | Chen et al. |
| 5,910,114 | A | * | 6/1999 | Nock et al. .................. 600/437 |
| 6,014,473 | A | * | 1/2000 | Hossack et al. .............. 382/294 |
| 6,409,668 | B1 | * | 6/2002 | Wollschlaeger ............. 600/443 |
| 6,425,867 | B1 | * | 7/2002 | Vaezy et al. ................. 600/439 |
| 6,454,714 | B1 | * | 9/2002 | Ng et al. ...................... 600/443 |
| 6,491,637 | B2 | * | 12/2002 | Foster et al. ................. 600/452 |
| 6,589,176 | B2 | * | 7/2003 | Jago et al. .................... 600/443 |
| 7,103,400 | B2 | * | 9/2006 | Ossmann et al. ............ 600/428 |
| 2005/0215904 | A1 | * | 9/2005 | Sumanaweera et al. ..... 600/458 |

OTHER PUBLICATIONS

"Kompendium Elektromedizin: Grundlagen, Anwendungen," Kresse (1978), pp. 231-232.
"A 2-D Acoustic Array for Diagnostic Imaging," Bechtold et al, IEEE Ultrasonics Symposium 1996, pp. 1573-1576.

* cited by examiner

*Primary Examiner*—Brian Casler
*Assistant Examiner*—Baisakhi Roy
(74) *Attorney, Agent, or Firm*—Schiff Hardin LLP

(57) ABSTRACT

In a method to generate a three-dimensional ultrasound image of a body region of a patient, spatially varying due to breathing motions, temporally successive B-images are generated with an ultrasonic transducer arrangement in a stationary image plane that, due to the breathing motion, pertain to various slice planes of the body region, and are combined dimensionally correctly with an image processing device into a 3D image.

3 Claims, 1 Drawing Sheet

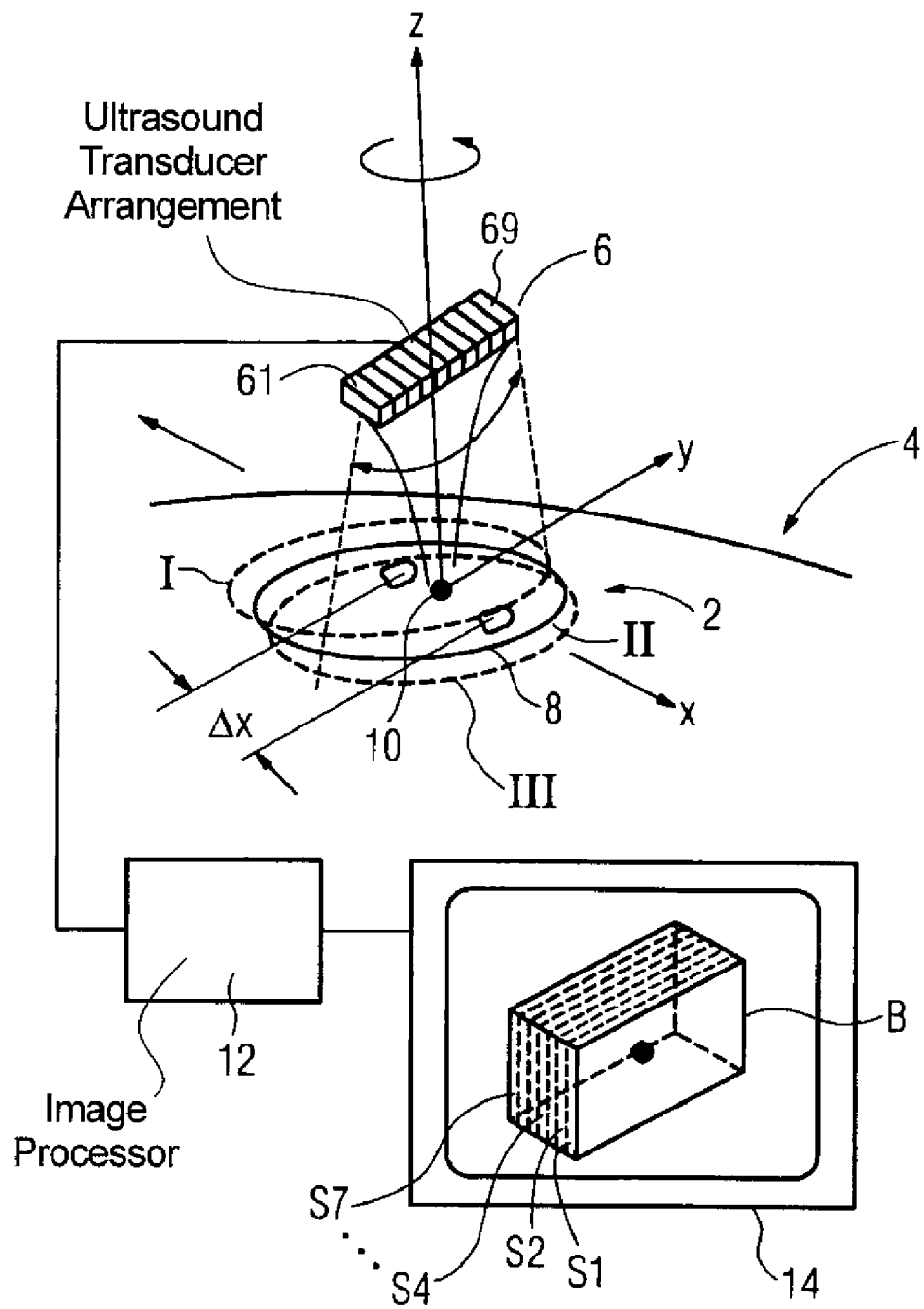

METHOD FOR GENERATING A THREE-DIMENSIONAL ULTRASOUND IMAGE

BACKGROUND OF THE INVENTION

1. Field of the Invention

The present invention concerns a method for generating a three-dimensional ultrasound image that is, in particular used in the monitoring and visualization of the disintegration of a calculus in lithotripsy.

2. Description of the Prior Art

During the course of a lithotripsy procedure for disintegrating, for example, a kidney stone, it is desirable to achieve the disintegration as efficiently as possible. This means that the fewest possible shockwave pulses should be applied to the patient, and the pulses should be applied in a manner that minimizes the discomfort to the patient. To assist in both of these goals, it is desirable to be able to visualize the successive disintegration of the calculus and its environment, after the application of each shockwave pulse, in a three-dimensional presentation.

Such a three-dimensional visualization is possible with a device as is known, for example, from M. Bechtold, B. Granz, R. Oppelt, "2-D Array for Diagnostic Imaging", IEEE Ultrasonics Symposium 1996, pages 1573-1576. The using a two-dimensional ultrasonic transducer arrangement of 64*64 transducer elements, a three-dimensional image is generated by phase-delayed control of transducer elements.

A three-dimensional ultrasound image also can be generated with a one-dimensional ultrasonic transducer arrangement, the transducer elements of which are controlled with phase-delays, and a B-image can be generated by electronic scanning (linear phased array). A series of two-dimensional images (B-image) is generated, with the images at respectively known scan positions, by a mechanical scanning perpendicular to the B-image plane. The series of these B-images is then combined into a three-dimensional image.

A method for generating a three-dimensional ultrasound image with a linear ultrasonic transducer array is known from German OS 98 28 947, in which the three-dimensional image is likewise composed of a number of B-images that arise in temporal succession given a movement of the linear ultrasonic transducer array. A dimensionally correct reproduction of a three-dimensional ultrasound image is also possible by means of a special evaluation of the temporally successive B-images when the movement ensues non-uniformly and, for example, is implemented manually by the operating personnel. Suitable commercial software for this purpose is available from Siemens AG under the trade name 3-Scape.

SUMMARY OF THE INVENTION

An object of the present invention is to provide a method to generate a three-dimensional ultrasound image that is structurally simple.

This object is achieved according to the invention by a method for generating with an ultrasonic transducer arrangement, a three-dimensional ultrasound image of a body region that is spatially varying due to breathing motions by generating temporally successive B-images in a stationary image plane. Due to the breathing motion, the B-images pertain to various slice planes of the body region. The B-images are combined, dimensionally correctly (i.e., with the images being in proper registration), with an image-processing device into a 3D image.

The invention is based on the recognition that just the shifting due to the breathing motion of the position of an internal body region of the patient relative to a stationary B-image plane is sufficient to generate a 3D image with a sequence of the B-images generated in a stationary image plane. The term "stationary", as used herein means that the B-scan plane (image plane) is either stationary relative to the treatment table or stationary relative to the body surface. Given a stationary arrangement relative to the body surface, the body region of the patient is also acquired in various slice planes due to the patient's breathing motion, since the body surface moves only slightly and primarily perpendicular to a surface normal due the breathing motion, while the internal organs experience primarily a motion transverse to the normal with a clearly larger movement range (up to 5 cm).

In order to be able to represent the maximum volume, the ultrasonic transducer arrangement and the scan plane or image plane associated therewith it must merely be positioned approximately perpendicular to the direction of the shifting caused by the breathing motion and be held in this position.

As an ultrasonic transducer arrangement, in particular an ultrasonic transducer array with a number of individually controllable transducer elements is used that enables a purely electronic generation of a B-image without mechanical motion. Suitable are, for example, a linear ultrasonic transducer array with which a linear scan can be implemented, or a curved linear array or a linear ultrasonic transducer array, controlled with phase-delays, that enable the implementation of electronic scanning.

Since a movement of the ultrasonic transducer arrangement is not necessary to generate a 3D image, a consistent ultrasound coupling is ensured, in particular given a direct arrangement of the transducer arrangement on the skin of the patient (image plane stationary relative to the body surface), such that fluctuations of the image quality of the individual B-images are prevented. Additionally, an unintentional tilting of the array, which would cause false planes to be shown in the body, is prevented.

In a further embodiment of the invention, the 3D image is converted into one or more C-images. This enables the consideration of the monitored body region in a type of representation as it is common in x-ray diagnostics, such that an x-ray image and the ultrasound image can be directly compared with one another. This manner presentation is very advantageous since the diagnostic contents of x-ray and ultrasound images can be used with a cumulative effect.

The method according to the invention is in particular used to monitor and visualize the disintegration of a calculus in lithotripsy. With the method the target precision in the disintegration procedure can be increased, meaning a precise adjustment of the focus of the shockwave on the calculus can be implemented. Moreover, a precise and clear monitoring of the disintegration of the calculus is possible, such that both the number of the shockwave pulses required for disintegration and the stress on healthy tissue zones can be reduced to a minimum. In this application, the device is preferably an integral component of a lithotripter.

DESCRIPTION OF THE DRAWINGS

The FIGURE illustrates an embodiment of the method according to the invention.

DESCRIPTION OF THE PREFERRED EMBODIMENTS

As shown in the FIGURE, an ultrasonic transducer arrangement 6 is positioned over a body region 2 to be examined of a patient 4 recumbent on a treatment table. The ultrasonic transducer arrangement 6 generates a B-image in a stationary zy plane. For this, during the image acquisition the ultrasonic transducer arrangement 6 is spatially fixed (stationary relative to a treatment table) and is applied to the skin surface of the patient 4 and acoustically coupled to it.

In the exemplary embodiment, as an ultrasonic transducer arrangement 6 a linear ultrasonic transducer array is provided with transducer elements 61-69 that are controlled in a phase-delayed manner. This can be arranged directly (coupled via a gel) on the skin surface of the patient 4, meaning stationary relative to the body surface of the patient. As an alternative to the use of such a phased array, a linear curved array or a linear array can also be provided with which a scanning or a linear scan can be implemented without a phase-delayed control of the transducer elements being necessary for this. In principle, ultrasonic transducer arrangements are also possible that generate a B-image with a mechanical motion, for example by mechanical scanning with an individual transducer.

It can be seen in the FIGURE that an examination subject located in the body region 2 (in the example a kidney 8 with a calculus 10 located therein) moves back and forth approximately linearly in a direction x due to the breathing motion of the patient 2, whereby the entire movement range $\Delta x$ can be up to 5 cm.

With the ultrasonic transducer arrangement 6, temporally successive B-images, meaning two-dimensional slice images from the body region 2 respectively located in the panning range of the ultrasonic transducer arrangement 6, are generated in the static (stationary) image plane zy with a predetermined repetition rate (for example 25 Hz).

In the FIGURE, the position of the kidney 8 and of the calculus 10 are shown dashed given respective maximum deflection, and shown continuously in a central position. During a complete breathing motion, a number of B-images S1 through S7 are generated (for clarity, only 7 B-images are drawn). The B-image S1 images a situation in which the kidney 8 is located in the dashed plotted position I. The region of the kidney is thereby acquired by the ultrasonic transducer arrangement 6, which is located at this point in time in the zy plane, meaning to the right of the calculus 10 in the FIGURE. The kidney 8 moves to the right in the x-direction, such that the static zy slice plane successively intersects other zones of the kidney 8. In the exposure of the B-image S4, the kidney 8 is located in position II and the calculus 10 is located in the zy plane, such that it is acquired by the ultrasonic transducer arrangement 6. In the exposure of the B-image S7, a region of the kidney 8 in the zy plane is acquired that lies left of the calculus 10 (position III).

In an image processor device 12, the successive B-images S1-S7 are combined dimensionally correctly into a 3D image that enables a spatial consideration of the appertaining body region on a monitor 14. The dimensionally correct combination of the individual B-images S1-S7 ensues according to a method as it is disclosed, for example, in German OS 198 28 947. Given combination of the B-images S1 through S7 accurate to side, a spatial image B of a section of the body region 2 around the calculus 10 arises, shown schematically as a cuboid.

In order to achieve a correct 3D reproduction, the scan plane zy of the ultrasonic transducer arrangement 6 must be aligned approximately perpendicular to the linear shifting of the body region 2 caused by the breathing motion. For this, for example, the array lengthwise direction (scan plane) is initially aligned in the direction of the breathing motion and the direction of the maximum displacement is determined. The array is subsequently rotated on the z-axis by 90° and then stands exactly perpendicular to the breathing motion.

Moreover, it is also possible with the image processing device 12 to undertake a C-image representation, meaning a representation in one or more projection planes perpendicular to the z-axis, meaning parallel to the xy plane.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating the three-dimensional ultrasound image of a body region of a patient, said body region exhibiting spatial variation due to breathing motion, comprising the steps of:

applying an ultrasound transducer arrangement to a body region of a patient exhibiting spatial variations due to breathing motion, and conducting an ultrasound scan of said region and maintaining said ultrasound transducer stationary on the body region to couple ultrasound radiation into the body region in a single stationary scan plane through which the body region moves due to said breathing motion, to obtain electrical signals respectively in different slice planes resulting from interaction of the ultrasound radiation with the body region moving through the single stationary scan plane;

from said electrical signals, generating temporally successive B-images of said body region, said successive B-images, due to said body region moving through said single stationary slice plane due to said breathing motion, respectively representing said different slice planes of the body region; and registrating the successive B-images and combining the registrated successive B-images in an image processor to form a three-dimensional image of said body region comprising said different slice planes, and making said three-dimensional image available in a form for display.

2. A method as claimed in claim 1 comprising employing an ultrasound transducer array as said ultrasound transducer arrangement.

3. A method as claimed in claim 1 comprising the additional step of converting said three-dimensional image of said body region into at least one C-image of said body region.

\* \* \* \* \*